United States Patent [19]
Ruest et al.

[11] 3,935,257
[45] Jan. 27, 1976

[54] CHEMICAL COMPOUNDS

[75] Inventors: Dennis A. Ruest, Manchester; C. Y. Shen, St. Louis; John L. Mason, University City, all of Mo.

[73] Assignee: Monsanto Company, St. Louis, Mo.

[22] Filed: Mar. 18, 1974

[21] Appl. No.: 452,307

[52] U.S. Cl........ 260/535 P; 260/340.6; 260/484 P
[51] Int. Cl.² ........................................ C07C 59/12
[58] Field of Search ................................ 260/535 P

[56] References Cited
UNITED STATES PATENTS
3,293,176 12/1966 While .............................. 260/535 P FOREIGN PATENTS OR APPLICATIONS
2,248,708 2/1972 Germany OTHER PUBLICATIONS
Noller, "Organic Chemistry," p. 170.

*Primary Examiner*—Lorraine A. Weinberger
*Assistant Examiner*—P. J. Killos
*Attorney, Agent, or Firm*—Neal E. Willis; J. E. Maurer; Thomas N. Wallin

[57] ABSTRACT

Compounds represented by the formula

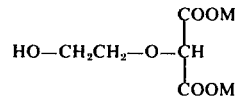

wherein M is alkali metal and acids thereof are useful intermediates for preparation of sequestrant compounds represented by the formula

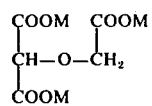

and acids thereof.

3 Claims, No Drawings

CHEMICAL COMPOUNDS

BACKGROUND OF THE INVENTION

This invention relates to novel compounds useful as intermediates for making ether tricarboxylates represented by the formula $$\begin{array}{c} COOM \quad COOM \\ | \quad\quad | \\ CH-O-CH_2 \\ | \\ COOM \end{array}$$

wherein M is an alkali metal acid of such ether tricarboxylates.

It is known that ether tricarboxylate salts, as represented by the above formula are useful as complexing agents and as detergency builders whereas the acid forms of such salts are useful intermediates for their production.

Although methods of making such compounds (e.g., via Williamson ether type synthesis) are known intermediates for preparing such compounds by alternate processes are desired.

SUMMARY OF THE INVENTION

This invention provides intermediates for preparation of the above-described ether tricarboxylates which intermediates are compounds represented by the formula $$\begin{array}{c} COOM \\ | \\ HO-CH_2CH_2-O-CH \\ | \\ COOM \end{array}$$

and acids thereof.

The compounds and their preparation and use will be understood from the following description of the preferred embodiments.

DESCRIPTION OF THE PREFERRED EMBODIMENTS

The compounds of this invention are 2-hydroxy ethoxy malonates represented by the formula $$\begin{array}{c} COOM \\ | \\ HO-CH_2CH_2-O-CH \\ | \\ COOM \end{array}$$

and acids thereof. (The acid forms of the 2-hydroxy ethoxy malonates generally exhibit the lactone structure

[structure: lactone ring with CH₂, CH₂, C=O, O, CHCOOH]

The 2-hydroxy ethoxy malonate $$\begin{array}{c} COOM \\ | \\ HO-CH_2CH_2-O-CH \\ | \\ COOM \end{array}$$

can be obtained by basic hydrolysis of p-dioxanone carboxylates represented by the formula

[structure: p-dioxanone ring with CH₂, CH₂, C=O, O, CHCOOM']

wherein M' is alkali metal or alkaline earth metal.

Although the p-dioxanone carboxylate has, for convenience, been represented above in keto structure and will hereinafter, in the specification and claims, be so represented, this representation is intended to encompass the enolate forms

[structure: enolate form, M' is divalent]   or   [structure: enolate form, M' is monovalent]

of such compounds.

As mentioned, reaction of the p-dioxanone carboxylate with aqueous alkali metal hydroxide will yield $$\begin{array}{c} COOM \\ | \\ HO-CH_2CH_2-O-CH \\ | \\ COOM \end{array}$$

If M of the p-dioxanone carboxylate is magnesium, it is generally desirable to first react the carboxylate with phosphoric acid and neutralize with ammonium hydroxide to form the ammonium carboxylate and separate solid $MgNH_4PO_4$. If desired, other salts can be obtained by converting the p-dioxanone ammonium carboxylate with the desired base and boiling to expel ammonia. The acid forms can be obtained by conventional acidulation techniques.

The p-dioxanone carboxylate can be prepared by carboxylation of the carbon atom of p-dioxanone adjacent to the C=O moiety of p-dioxanone (which can be prepared by dehydrogenation of diethylene glycol according to methods described in U.S. Pat. Nos. 2,900,395 and 3,119,840, the disclosure thereof being incorporated herein by reference).

In one suitable technique, p-dioxanone is carboxylated by reaction with lithium diisopropyl amide (the reaction preferably being conducted in a solvent such as tetrahydrofuran at temperatures of from −40° to −80°C.) followed by reaction with gaseous carbon dioxide at temperatures of from −20° to −70°C.

The p-dioxanone can also be carboxylated by reaction with methyl methoxy magnesium carbonate. This reaction is most conveniently conducted in a solvent (e.g., an equal parts by weight mixture of dimethylformamide and bis-2-methoxy ethyl ether using an excess of methyl methoxy magnesium carbonate at a temperature of from 100° to 160°C.

The 2-hydroxy-ethoxy malonates

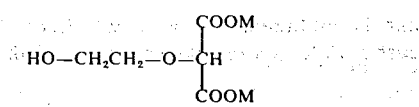

and the acid forms thereof can be oxidized to yield compounds represented by the formula

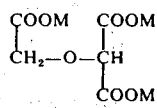

and acids thereof having utilities previously discussed.

The choice of salt or acid form of the 2-hydroxy ethoxy malonate and oxidation conditions (acidic or basic) will determine whether the salt or acid form of the ether tricarboxylate is obtained. The salts of acid ether tricarboxylate forms can, of course, be converted to other forms by conventional acidification, esterification or neutralization procedures.

The oxidation can be accomplished by any suitable technique.

For example, the oxidation can be accomplished using potassium permanganate as an oxidizing agent. This oxidation reaction is preferably conducted in an aqueous system at temperatures of from 25° to 65°C, most preferably, 45° to 60°C. The permanganate can be added as a solution or solid. Preferably, to optimize yields, the permanganate is added as a solid in an amount equal to from 2% to 30% by weight of the hydroxy ethoxy malonate solution and at least stoichometrically equivalent to oxidize the hydroxy ethoxy malonate. It is generally preferred to conduct this oxidation in basic medium (pH 9–12) to inhibit decarboxylation and, when ether tricarboxylate salt is desired, to obviate the need for a separate neutralization step.

In another technique, oxidation is accomplished using $CrO_3$ (preferably from 1 to 1.5 mole $CrO_3$ per mole of $-CH_2OH$ group equivalent) dissolved in sulfuric acid. The oxidation is preferably conducted at temperatures below 50°C to avoid excessive decarboxylation. The reaction product is the acidic form of the ether tricarboxylate which can be esterified by conventional techniques and separated (in ester form) from chromium sulfate by extraction with a solvent such as chloroform. The ester can, if desired, be converted to the salt form by reaction with alkali metal hydroxide.

The invention is further illustrated by the following examples wherein all parts and percentages are by weight unless otherwise indicated.

EXAMPLE I

A solution of 0.07 moles methyl methoxy magnesium carbonate in 50 ml. of a 3:1 mixture of bis-2-methoxy ethyl ether/dimethylformamide is prepared and heated to 110°C under nitrogen atmosphere. A solution of 0.05 moles p-dioxanone in 12.5 ml. dimethylformamide is added and the temperature raised to 150°C. The mixture is maintained at this temperature for 4 hours, cooled to 50°C, poured into 200 ml. ethyl ether, and filtered to separate solid

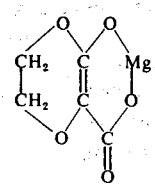

product.

This product is dissolved in a solution of 0.07 mole $H_3PO_4$ in 150 ml. water. The resulting solution is neutralized to pH 9.5 with concentrated ammonium hydroxide and filtered to remove solid $MgNH_4PO_4 6H_2O$. The filtrate is passed through a column of acidic ion exchange resin (identify by other than Amberlyst trade name) and neutralized with sodium hydroxide to yield

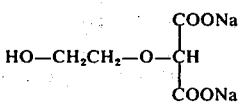

A solution of 10 grams

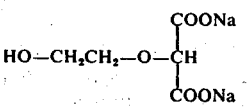

in 40 ml. deionized water is prepared and sodium hydroxide added to adjust solution pH to about 11.5. The solution is heated to about 50°C and 12.1 grams of solid potassium permanganate added over a 90 minute period, the pH being maintained at 11.9 by sodium hydroxide addition. The reaction mixture is filtered through a fritted glass funnel and the filtrate is evaporated to leave a solid

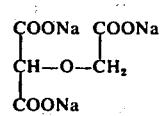

residue.

EXAMPLE II

A mixture of 4.2 grams n-butyl lithium in 35 ml. hexane is added to a mixture of 6 grams diisopropyl amine in 60 ml. tetrahydrofuran precooled to about −35°C. The mixture is then cooled to −75°C and a solution of 6.12 grams p-dioxanone in 40 ml. tetrahydrofuran is added dropwise. Gaseous carbon dioxide is then bubbled through the mixture for one hour.

The solvents are evaporated, leaving a solid product containing

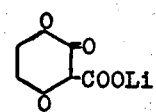

which is dissolved in water, acidified to pH 2.7 with hydrochloric acid. Sodium hydroxide is added to raise the pH to 12.3 and methanol is added into the mixture to crystallize

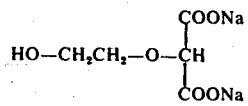

A solution of 28.6 milliequivalents of this compound in 125 ml. water is admixed with 1.2 grams of catalyst consisting of 5% platinum on a carbon support. The temperature is raised to 80°C and oxygen bubbled into the mixture at a rate of 600 cc. per minute for a period of about 12 hours. The pH is maintained between 9 and 10 by periodic addition of NaOH. The catalyst is separated from the resulting solution of

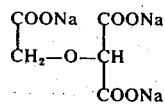

by filtration.

EXAMPLE III

About 0.0557 mole $(NaO_2C)_2CH-O-CH_2CH_2OH$ is dissolved in 25 ml. 30% $H_2SO_4$ and cooled to 0°C. To this solution a mixture of 8.1 grams $CrO_3$ and 60 grams 40% $H_2SO_4$ is added. The temperature of the reaction mixture is gradually raised to about 25°C and maintained at that temperature for 30 minutes. The reaction mixture is diluted with 100 ml. ethanol and most of the chromium sulfate removed by filtration. The ethanol solution is vacuum concentrated, and neutralized with a dilute $Na_2CO_3$ solution. The solution is then extracted with chloroform to recover the ester

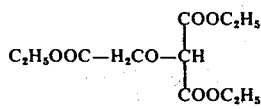

The chloroform is removed by evaporation and the ester is added to boiling NaOH to yield

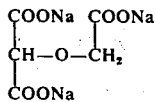

What is claimed is:
1. Compounds represented by the formula

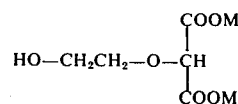

wherein M is alkali metal, and acids thereof.

2. A compound according to claim 1 represented by the formula

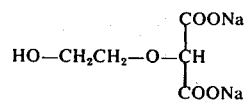

3. A method of making compounds represented by the formula

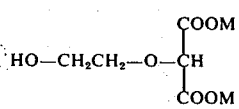

wherein M is alkali metal and acids thereof, said method comprising reacting a compound represented by the formula

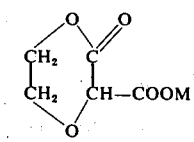

wherein M' is alkali metal or alkaline earth metal with an alkali metal hydroxide to yield

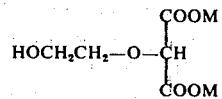

and, when the acid form thereof is desired, acidulating said

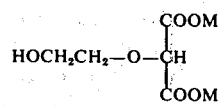

* * * * *

UNITED STATES PATENT OFFICE
CERTIFICATE OF CORRECTION

PATENT NO. : 3,935,257
DATED : January 27, 1976
INVENTOR(S) : Dennis A. Ruest et al It is certified that error appears in the above-identified patent and that said Letters Patent are hereby corrected as shown below:

Column 6, line 30,

"
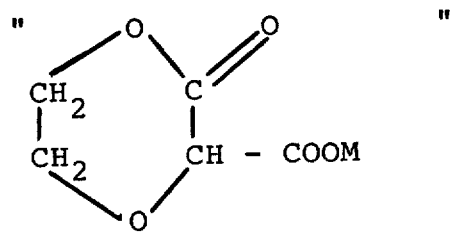
"

should be ---

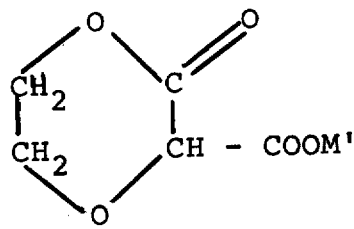

---.

Signed and Sealed this twenty-second Day of June 1976

[SEAL]

Attest:

RUTH C. MASON
Attesting Officer

C. MARSHALL DANN
Commissioner of Patents and Trademarks